United States Patent [19]

Michaelson

[11] 4,414,198

[45] Nov. 8, 1983

[54] RAPIDLY DISINTEGRABLE TABLET COMPOSITION AND METHOD

[76] Inventor: Joseph Michaelson, 4767 Elmer Ave., North Hollywood, Calif. 91602

[21] Appl. No.: 371,517

[22] Filed: Apr. 23, 1982

[51] Int. Cl.³ .......................... A61K 9/26; A61K 9/36; A61K 9/62; A61K 9/04

[52] U.S. Cl. ......................................... 424/44; 424/22; 424/35; 426/86; 426/590; 426/591; 426/594

[58] Field of Search ............................ 424/22, 35, 44; 426/590, 591, 594, 86

[56] References Cited

U.S. PATENT DOCUMENTS

| | | | |
|---|---|---|---|
| 2,889,226 | 6/1959 | Hinkley | 426/591 |
| 3,903,255 | 9/1975 | Gusman | 424/44 |
| 4,079,125 | 3/1978 | Sipos | 424/35 X |
| 4,172,120 | 10/1979 | Todd | 424/44 |
| 4,344,968 | 8/1982 | Aoda | 424/22 X |

*Primary Examiner*—Stanley J. Friedman
*Attorney, Agent, or Firm*—Wagner & Bachand

[57] ABSTRACT

Rapidly water-disintegrable tablet is provided comprising an active ingredient such as a foodstuff or medicament, and distributed therewithin a small but effective amount of a tablet disintegrable system comprising an unreacted, intimate mixture of alginic acid and a water soluble metal carbonate in proportions reactive to form metal alginic acid salt and carbonic acid when the tablet is placed in water, the bulk of the salt acting to swell the tablet and the carbonic acid acting to simultaneously release carbon dioxide within the swelling tablet whereby rapid disintegration of the tablet is effected.

19 Claims, No Drawings

RAPIDLY DISINTEGRABLE TABLET COMPOSITION AND METHOD

TECHNICAL FIELD

This invention has to do with tablet compositions for the rapid generation of liquid products of high organoleptic quality and excellent body for enhanced consumer appeal.

More particularly, the invention is concerned with improvements in tablet compositions of the type comprising in addition to the active ingredient such as a foodstuff, medicament and the like, binder and excipient, a novel disintegrant system, of food grade constitution which simultaneously bulks the tablet from within and releases carbon dioxide gas for rapid disintegration of the tablet and release of the active ingredients, with in situ generation of thickening agent to increase apparent body of the liquid produced, for increased consumer acceptance, and without use of organoleptically offensive acids such as tartaric and citric or their salts.

BACKGROUND ART

The art of tablet making involves the making of a composition which is readily compressible, sturdy for packaging and handling, and disintegrable in a predictable manner. Speed of compression to an integral tablet is achieved by the use in the tablet, in addition to use of the active ingredient, a binder, and an excipient, of a lubricant which facilitates release of the powders from the molds in which the tablets are formed and from the dies and punches which ram the powders into the molds. In general, present lubricants are insoluble in water and will leave a residue after tablet disintegration, at a cost of consumer appeal in a transparent product such as coffee, tea and clear soups. For rapid disintegration tablets are compounded with disintegrants which as their name implies act to disintegrate the tablet under predetermined conditions. Disintegrants heretofore used include corn starch, alginic acid, celluloses, and polyvinyl pyrrolidone.

Lubricants heretofore used include talcum powder, magnesium stearate, calcium stearate, vegetable stearin, stearic acid, Carbowax (trademark), and the like. Leucine has been referred to as a lubricant, (Remington's Practice of Pharmacy, 12th Edition, 1961, at page 448) but no use thereof is known to applicant in combination with any particular product and/or disintegrating system, and particularly not previously known is the use of a leucine with the present disintegrating system. Such use is novel and provides unexpected benefits in that leucine is an amino acid and thus biologically acceptable in foodstuffs, is water soluble and thus leaves no residue, and has a highly palatable taste in liquids produced therewith, in addition to being a fine lubricant for tablet compositions. Thus, leucine, together with the disintegrating system disclosed herein, enables an organoleptically and esthetically pleasing, residue-free water reconstitution of foodstuffs such as beverages ranging from soft drinks to coffee, tea, cocoa, and soups, as well as of medications, e.g. those which are taken orally, such as asprin and antacid products.

DESCRIPTION OF THE INVENTION

It is therefore an object of the invention to provide a new and superior tablet composition having a disintegrant system enabling rapid disintegration in water, and such compositions using lubricants as well. It is another object to provide tablets comprising an active ingredient such as a foodstuff or medicament, and a disintegrant which has dual action when the tablet is exposed to water, with the production of a by-product which acts to body the solution. It is a highly particular object to provide tablets including a food grade disintegrating system comprising biologically benign components or organoleptically desirable qualities.

These and other objects of the invention to become apparent hereinafter are realized in a rapidly water-disintegrable tablet comprising an active ingredient, and distributed therewithin a small but effective amount of a tablet disintegrating system comprising an unreacted, intimate mixture of alginic acid and a water soluble carbonate radical precursor in proportions reactive to form alginic acid salt and carbonic acid when the tablet is placed in water, the bulk of the formed salt acting to swell the tablet and the carbonic acid acting to simultaneously release carbon dioxide within the swelling tablet whereby rapid disintegration of the tablet is effected, said alginic acid salt acting to body the resulting active ingredient solution.

In particular embodiments, the active ingredient is a medicament, or a foodstuff including beverages.

Additionally, typically the weight ratio of the carbonate radical precursor to the alginic acid is three or more; the alginic acid is present in an effective amount between 0.05 and 25% by weight based on the weight of the tablet; and the metal carbonate is a carbonate or bicarbonate of an alkali or alkaline earth metal, such as the metals sodium, potassium, calcium, magensium or managnese.

In further embodiments the tablet further comprises a tablet-lubricating effective amount of a lubricant, e.g. a water soluble tablet lubricant comprising leucine in tablet-lubricating effective amount, e.g. L-leucine or L-isoleucine.

In particularly preferred embodiments, the invention provides a rapidly water-disintegrable tablet comprising an active ingredient, and distributed therewithin an effective amount of a tablet disintegrating system comprising an unreacted, intimate mixture of alginic acid and a water soluble metal carbonate in proportions reactive to form metal alginic acid salt and carbonic acid when the tablet is placed in water, said alginic acid comprising from 3 to 15% and the metal carbonate from 1 to 70% of the tablet by weight, the bulk of the salt formed acting to swell the tablet and the carbonic acid acting to simultaneously release carbon dioxide within the swelling tablet whereby rapid disintegration of the tablet is effected, the alginic acid salt acting to body the resulting active ingredient solution.

In this embodiment typically the metal carbonate is a carbonate or bicarbonate of an alkali metal, e.g. sodium or potassium; the active ingredient is a foodstuff or medicament; the tablet further comprises a lubricating effective amount of a lubricant, e.g. a tablet lubricant comprising L-leucine or L-isoleucine in an amount between 0.1 and 5 parts, and especially between 0.3 and 1.5 parts per 10 parts by weight of the tablet particularly where the active ingredient is coffee; and preferably the carbonate is sodium bicarbonate and is present in about stoichiometric amount for reaction with the alginic acid.

The invention further contemplates provision of a method of preparing a rapidly water-disintegrable tablet, including combining an active ingredient with a small but effective amount of an unreacted mixture of a water soluble carbonate radical precursor and alginic acid intimately and under pressure, pulverizing, and tabletting with a lubricant such as L-leucine or L-isoleucine in lubricating effective amount as necessary to form a stable tablet.

PREFERRED MODES

The tablets embodying the present invention comprise an active ingredient, typically powdered, or made into a powder by combination with a solid or removal synthetically of the water therein, which has therapeutic, nutritious, or medicinal qualities, for example, which it is desired to package in tabletted form. The active ingredient can be combined with excipients, binders, bulking agents, lubricants, processing aids, dyes and colorants, and other expedients normally used in tablet manufacture. In general these additives are used in their conventional amounts for their known purposes, and are selected so as to not interfere with the desirable organoleptic values, residue-free esthetic advantages and in situ bodying properties resultant from use of the present invention in constituting the tablet.

The method of combining the ingredients is conventional, with all parts being reduced or increased to a suitably tabletable particle size, and intimately mixed as necessary for the desired degree of uniformity in the tablet composition. In a final stage, the tablet is formed by a punch or die acting with a suitable cavity.

To conventional composition and processing the present invention brings an improved disintegrating system. The system comprises alginic acid, a commercially available material widely used in tablet making as a disintegrant, without however, the generation of carbon dioxide as well. To the tablet composition of active ingredient, excipient if any, and alginic acid, a carbonate radical ($CO_3^{--}$) precursor is added in accordance with the invention. The function of the carbonate radical precursor is to generate carbon dioxide responsive to neutralizing reaction of the carbonate radical precursor with the alginic acid.

Suitable sources of carbonate radicals are the alkali and alkaline earth metal salts of carbonic acid, e.g. sodium, potassium, calcium, magnesium or manganese carbonates and bicarbonates, which are effective precursors of the carbonate radical in that they form carbonate radicals when exposed to water, as the tablets of the invention are. The proportions of carbonate radical precursor and alginic acid are desirably stoichiometric, i.e. three parts of carbonate radical per part of alginic acid, but can be more or less provided carbon dioxide evolution is realized by the combination of the alginic acid and carbonate radicals into carbonic acid, together with by-product water and alginic acid salt. The alginic acid salt, e.g. sodium alginate, is produced in situ in the solution is a known thickening agent, and contributes a bodying quality to the solution.

In a typical tablet according to the invention, there is used from 0.05 to 25% by weight of the alginic acid, and the mentioned stoichiometric amount or more of the carbonate radical precursor. In a particular product useful for foodstuffs, the alginic acid comprises from 3-15% of the tablet by weight and a metal carbonate, such as sodium bicarbonate, from 1 to 70% of the tablet, the balance being active ingredient and any other formulation expedients desired.

As noted above, L-leucine or isoleucine is advantageously used as a lubricant in tablets according to the invention, e.g. in amounts of from 0.1 to 5, and more particularly from 0.3 to 1.5 parts, especially for instant coffee tablets prepared in accordance with the invention, or more or less amount that is effective for easing tablet formation and release from forming tools. The leucines are noteworthy in being water soluble in water sufficient to dissolve the tablets being described, so that upon addition to water, there is no solid residue, and a highly esthetic food or medicinal product can be obtained. Further, the leucines are essentially amino acids, so they are biologically safe.

EXAMPLE 1

Instant Coffee Tablet

A tabletted form of instant coffee was prepared by combining previously prepared powdered, e.g. instant coffee granules of suitable size for tabletting by combining for each tablet

| | |
|---|---|
| 12.5 gm. | powdered coffee |
| 1.0 gm. | alginic acid |
| 3.0 gm. | sodium bicarbonate |
| 0.7 gm. | L-leucine | slugging and grinding to about 40–60 U.S. Mesh.

This intermediate was blended with 1.0 gm. of a 3:1 weight mixture of sodium bicarbonate and alginic acid, and 1.0 gm. of L-leucine. Tablet formation was effected in a conventional tabletter with each tablet weighing about 17.4 gms., as necessary to prepare approximately 1 cup of coffee.

Coffee preparation involved depositing the tablet in very hot water. A fizzy evolution of carbon dioxide gas and ubiquitous fragmentation of the tablet occurred with rapid distribution of the coffee through the cup water. A sweet tasting beverage with seemingly enhanced body was noted. Also, inspection of the cup revealed no residue. In a CONTROL the procedures of the Example are varied by omitting the alginic acid and substituting a like amount of pre-prepared sodium alginate, Control I; or by omitting the sodium bicarbonate, Control II. In each instance tablet disintegration is markedly slower, stirring is required to fully break up the tablet, and the body of the beverage is thinner and less satisfactory. It is thus demonstrated that the carbonate alone is inferior to the combination of alginic acid and carbonate, and that pre-prepared sodium alginate as a disintegrant is inferior to that generated in situ by reaction of alginic acid and carbonate. This synergistic result is entirely unexpected.

EXAMPLE 2

Example 1 is repeated omitting the leucine. Tablet performance is equivalent but the resultant coffee is less sweet tasting. Tea, cocoa, and soups can be similarly prepared.

EXAMPLE 3

Reconstituted Milk

A powdered milk tablet is prepared substituting powdered milk for the coffee in Example 1, and reducing the L-leucine to 0.5 gm. before slugging and 300 mg. after, per tablet. On combination with cold water, the tablet disintegrates with a self-stirring evolution of gas. A wholesome tasting milk is obtained. Enhanced body over other reconstituted milk is noted, apparently by virtue of the presence of sodium alginate.

EXAMPLE 4

Asprin

A composition of

| | |
|---|---|
| 325 mg. | acetylsalicylic acid |
| 30 mg. | starch |
| 210 mg. | disintegrant (1:3 alginic acid: potassium carbonate) | was tabletted. Dropping the tablets in water results in immediate dissolution with outgassing, fragmentation of the tablets, and no residue.

EXAMPLE 5

Vitamin C

A vitamin preparation is prepared from

| | |
|---|---|
| 225 mg. | ascorbic acid |
| 125 mg. | disintegrant (1:4 alginic acid: magnesium carbonate) |
| 40 mg. | leucine |

Tablet formation is easy, and disintegration in aqueous medium rapid.

There is thus provided a novel disintegration system for tablet versions of foodstuffs, medicaments, and like active ingredient products available or potentially available in less convenient powders. The disintegrant not only breaks up the tablet by a combination of gas production and bulking, but as well generates an alginate salt useful per se as a bodying agent so the liquid product is enhanced in consumer appeal.

I claim:

1. Rapidly water-disintegrable tablet comprising an active ingredient, and distributed therewithin a small but effective amount of a tablet disintegrable system comprising an unreacted, intimate mixture of alginic acid and a water soluble carbonate radical precursor in proportions reactive to form metal alginic acid salt and carbonic acid when the tablet is placed in water, the bulk of said formed salt acting to swell the tablet and the carbonic acid acting to simultaneously release carbon dioxide within the swelling tablet whereby rapid disintegration of the tablet is effected, the alginic acid salt acting to body the resulting active ingredient solution.

2. The rapidly water-disintegrable tablet according to claim 1, in which said active ingredient is a medicament.

3. The rapidly water-disintegrable tablet according to claim 1 in which said active ingredient is a foodstuff.

4. The rapidly water-disintegrable tablet according to claim 1, in which the weight ratio of said carbonate radical precursor to said alginic acid is three or more.

5. The rapidly water-disintegrable tablet according to claim 4, in which said alginic acid is present in an effective amount between 0.05 and 25% by weight based on the weight of said tablet.

6. Rapidly water-disintegrable tablet according to claim 1, in which said carbonate radical precursor is a carbonate or bicarbonate of an alkali or alkaline earth metal.

7. Rapidly water-disintegrable tablet according to claim 6, in which said metal is sodium, potassium, calcium, magensium or managnese.

8. Rapidly water-disintegrable tablet according to claim 1, in which the tablet further comprises a tablet-lubricating effective amount of a lubricant.

9. Rapidly water-disintegrable tablet according to claim 8, in which the tablet lubricant comprises leucine in tablet-lubricating effective amount.

10. Rapidly water-disintegrable tablet according to claim 9, in which the leucine is L-leucine or L-isoleucine.

11. Rapidly water-disintegrable tablet comprising an active ingredient, and distributed therewithin an effective amount of a tablet disintegrable system comprising an unreacted, intimate mixture of alginic acid and a water soluble metal carbonate in proportions reactive to form metal alginic acid salt and carbonic acid when the tablet is placed in water, said alginic acid comprising from 3 to 15% and the metal carbonate from 1 to 70% of the tablet by weight, the bulk of the salt formed acting to swell the tablet and the carbonic acid acting to simultaneously release carbon dioxide within the swelling tablet whereby rapid disintegration of the tablet is effected, said alginic acid salt acting to body the resulting active ingredient solution.

12. Rapidly water-disintegrable tablet according to claim 11, in which the metal carbonate is a carbonate or bicarbonate of an alkali metal.

13. Rapidly water-disintegrable tablet according to claim 12, in which the metal is sodium or potassium.

14. Rapidly water-disintegrable tablet according to claim 11, in which the active ingredient is a foodstuff or medicament.

15. Rapidly water-disintegrable tablet according to claim 14, in which said tablet further comprises a tablet-lubricating effective amount of a lubricant.

16. Rapidly water-disintegrable tablet according to claim 15, in which said tablet lubricant comprises L-leucine or L-isoleucine in an amount between 0.3 and 1.5 parts per 10 parts by weight of said tablet.

17. Rapidly water-disintegrable tablet according to claim 14, in which the carbonate is sodium bicarbonate and is present in about stoichiometric amount for reaction with said alginic acid.

18. Method of preparing a rapidly water-disintegrable tablet, including combining an active ingredient with a small but effective amount of an unreacted mixture of a water soluble metal carbonate and alginic acid, intimately and under pressure, pulverizing, and tabletting with a lubricant as necessary to form a stable tablet.

19. Method according to claim 18, including also incorporating L-leucine or L-isoleucine as said lubricant, in lubricating effective amount in advance of the tabletting step.

* * * * *